(12) United States Patent
Ruangwattanasuk

(10) Patent No.: US 10,576,092 B1
(45) Date of Patent: Mar. 3, 2020

(54) DOXORUBICIN DERIVATIVES AND USES THEREOF

(71) Applicants: S.S.Manufacturing Co. Ltd, Nonthaburi (TH); Ornin Ruangwattanasuk, Bangkok (TH)

(72) Inventor: Ornin Ruangwattanasuk, Bangkok (TH)

(73) Assignees: S.S. MANUFACTURING CO. LTD., Nonthaburi (TH); Ornin Ruangwattanasuk, Bangkok (TH)

(*) Notice: Subject to any disclaimer, the term of this patent is extended or adjusted under 35 U.S.C. 154(b) by 0 days.

(21) Appl. No.: 16/281,303

(22) Filed: Feb. 21, 2019

(51) Int. Cl.
| | |
|---|---|
| *A61K 31/56* | (2006.01) |
| *A61P 35/00* | (2006.01) |
| *A61K 31/58* | (2006.01) |

(52) U.S. Cl.
CPC ............... *A61K 31/58* (2013.01); *A61P 35/00* (2018.01)

(58) Field of Classification Search
CPC ..................................................... A61K 31/56
USPC ......................................................... 514/182
See application file for complete search history.

(56) References Cited

U.S. PATENT DOCUMENTS

| | | | |
|---|---|---|---|
| 8,354,116 B2 * | 1/2013 | Carter | C07C 69/612 424/400 |
| 2007/0275911 A1 * | 11/2007 | Koch | C07D 215/56 514/34 |

* cited by examiner

*Primary Examiner* — Raymond J Henley, III
(74) *Attorney, Agent, or Firm* — Moser Taboada

(57) ABSTRACT

This invention relates to molecule and methods of treating diseases and disorders utilizing a Compound: ((3bS)-7-hydroxy-11a-methyl-1H,2H,3H,3aH,3bH,4H,5H,9bH,10H,11H,11aH-cyclopenta[a]phenanthren-1-yl N-[(2S,3S,6R)-3-hydroxy-2-methyl-6-{[(1S,3S)-3,5,12-trihydroxy-3-(2-hydroxyacetyl)-10-methoxy-6,11-dioxo-1,2,3,4,6,11-hexahydrotetracen-1-yl]oxy}oxan-4-yl]carbamate) and pharmaceutically acceptable salts, hydrates, solvates, clathrates, prodrugs and polymorphs thereof. The present invention encompasses the in vitro and in vivo use of the said compound and the incorporation of the said compound into pharmaceutical compositions for the treatments and preventions of a variety of diseases and disorders.

2 Claims, 3 Drawing Sheets

DOXORUBICIN DERIVATIVES AND USES THEREOF

FIELD OF THE INVENTION

This invention relates to Doxorubicin derivatives and the uses thereof.

BACKGROUND OF THE INVENTION

The prodrug approach to modifying pharmaceuticals in order to overcome one or more undesirable properties of the parent drug has been studied and applied to many compounds in clinical use today. The prodrugs formed are often intended to modify the absorption, metabolism, excretion, toxicity or activity of the parent compound in a desirable way. Additionally, prodrug modifications have been made to some compounds with the goal of creating a drug that is selectively activated or deactivated in a target tissue to increase the specificity of the intended drug effects while decreasing the unintended side effects associated with the parent compound. The prodrug approach has been applied to some of the most successful antibiotics and chemotherapeutic compounds that are designed to be toxic to some living cells and simultaneously non-toxic or much less toxic to other populations of living cells. For example, Doxorubicin (DOX) (CAS No. 25316-40-9) is known as an effective and the most widely used chemotherapeutic agent that has multi-modal cytotoxicity (1-2). Several DOX derivatives have been constructed to date in which those derivatives have demonstrated additional different properties when compared to DOX. Although several derivatives have been found to exhibit greater cytotoxicity than the clinically used anthracyclines, a concomitant increase in systemic toxicity is also commonly observed.

It has been known that Doxorubicin accumulates in cell nuclei. The main cytotoxic actions of doxorubicin occur in the nucleus. After administration, doxorubicin diffuses into cell cytoplasm and enters the nucleus where it binds to topoisomerase and intercalates to the DNA strand. Both nucleolar actions are regarded as the major cytotoxic actions of doxorubicin as well as other anthracycline derivatives (3-5). In addition to nucleolar-specific action, doxorubicin also has multiple cytotoxic actions, especially oxidative stress generation (6-9). However, considering the effects of subcellular distribution of DOX derivatives, it is desirable to have a new derivative having considerable cytotoxicity that can be prevented from entering into the cell nucleus.

It has also been known that bio-conjugation is a process used to attach a bioactive molecule to another molecule via a covalent bond which leads to the formation of a novel chemical structure which may have enhanced properties compared to those of the original molecule. While this process or method has been known, there has not been an attempt in synthesizing a derivative that is capable of functioning as per the need as above mentioned.

SUMMARY OF THE INVENTION

This invention relates to the molecule and methods of treating diseases and disorders utilizing a new derivative of DOX that was derived via conjugation of the 3' amino group of DOX to the estradiol having the compound formula as ((3bS)-7-hydroxy-11a-methyl-1H,2H,3H,3aH,3bH,4H,5H,9bH,10H,11H,11aH-cyclopenta[a]phenanthren-1-yl N-[(2S,3S,6R)-3-hydroxy-2-methyl-6-{[(1S,3S)-3,5,12-trihydroxy-3-(2-hydroxyacetyl)-10-methoxy-6,11-dioxo-1,2,3,4,6,11-hexahydrotetracen-1-yl]oxy}oxan-4-yl]carbamate). In one aspect, pharmaceutical compositions comprising the disclosed compound cover an enantiomer of the said compound and pharmaceutically acceptable polymorphs, prodrugs, hydrates, solvates, salts, hydrates, clathrates, and solvates thereof.

The conjugated product rapidly induced MCF-7 cell apoptosis without entering the nucleus and thus can address the aforementioned needs. Thus, the primary objective of use is for cancer treatment. Cancers in this case include, but are not limited to, cancer of the head, thyroid, neck, eye, skin, mouth, throat, esophagus, chest, heart, bone, blood, bone marrow, lung, colon, sigmoid, rectum, stomach, prostate, breast, ovaries, kidney, liver, pancreas, brain, intestine, heart, adrenal, subcutaneous tissue, lymph nodes, heart, and combinations thereof. More specifically, specific types of cancers that can be treated using this compound include multiple myeloma, malignant melanoma, malignant glioma, leukemia, and solid tumors.

The conjugated product shows higher solubility in fat solvent therefore the application of use may suitable for but are not limited to an emulsion formulation, topical formulation and chemoembolization.

The invention has broad applicability to many different therapeutic drugs, as well as to a variety of diseases and conditions. In the other aspect, the stereometically pure disclosed compound is also useful in the treatment or prevention of microbial infections or the symptoms of microbial infections including, but not limited to, bacterial infections, fungal infections, malaria, mycobacterial infection, and opportunistic infections resulting from HIV.

Some embodiments disclosed herein relate to a pharmaceutical compound comprising a first component as doxorubicin and a second component as estradiol, wherein the first component is covalently conjugated to the second component having a structure represented by the following chemical formula (I):

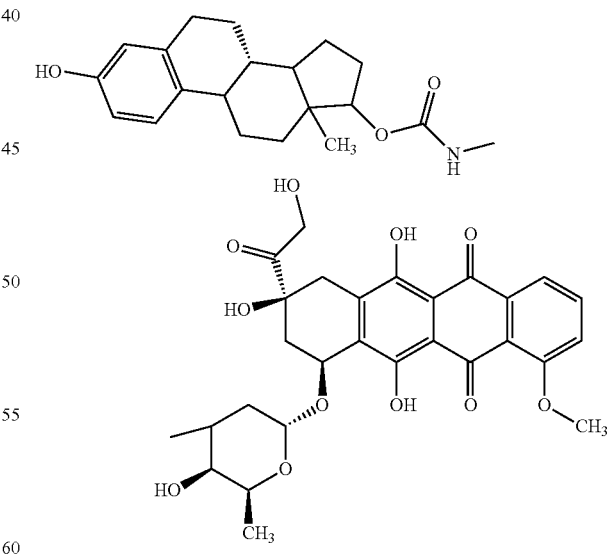

wherein the 3' amino group of doxorubicin is conjugated to estradiol.

Some embodiments disclosed herein relate to a pharmaceutical compound comprising a compound as defined above and a pharmaceutically acceptable carrier, excipient and/or adjuvant.

Some embodiments disclosed herein relate to use of the compound as defined above in medicine, such as the use of the embodied compound in a medicament. In some embodiments disclosed herein, the medicament including the compound as defined herein is suitable for treating mammals, such as a human.

Some embodiments disclosed herein relate to use of the compound as defined above for the manufacture of a medicament for the treatment of a cancer comprising cancer cells. Examples of the cancer include breast cancer, ovarian, cervical, and other estrogen-receptor-positive (ER+) cancers.

BRIEF DESCRIPTIONS OF THE DRAWINGS

DETAILED DESCRIPTION OF THE INVENTION

Various aspects of the present invention are described in detail in the following, each attached as an individual Example. The Examples are provided for the purpose of illustration and are not intended to limit the scope of the present invention.

This invention relates to molecule and methods of treating diseases and disorders utilizing a Compound: ((3bS)-7-hydroxy-11a-methyl-1H,2H,3H,3aH,3bH,4H,5H,9bH,10H,11H,11aH-cyclopenta[a]phenanthren-1-yl N-[(2S,3S,6R)-3-hydroxy-2-methyl-6-{[(1S,3S)-3,5,12-trihydroxy-3-(2-hydroxyacetyl)-10-methoxy-6,11-dioxo-1,2,3,4,6,11-hexahydrotetracen-1-yl]oxy}oxan-4-yl]carbamate) and pharmaceutically acceptable salts, hydrates, solvates, clathrates, prodrugs and polymorphs thereof. It was found that transferrin-conjugated DOX that was modified at the 3' amino group was also found to be unable to enter the nucleus.

The present invention encompasses the in vitro and in vivo use of the said compound and the incorporation of the said compound into pharmaceutical compositions for the treatments and preventions of a variety of diseases and disorders. Such treatments include, particularly, the inhibition of tumor cell proliferation, the treatment or prevention of cancer, including, but not limited to, solid tumors, blood-born tumors, leukemias, and in particular, multiple myeloma.

The pharmaceutical composition comprising the disclosed compound is adjunctively administered with at least one additional therapeutic agent. Examples of additional therapeutic agents include, but are not limited to, anti-cancer drugs, anti-inflammatories, antihistamines, and decongestants.

According to one aspect of the disclosure, a pharmaceutical compound comprising a first component as doxorubicin and a second component as estradiol is disclosed, wherein the first component is covalently conjugated to the second component having a structure represented by the following chemical formula (I):

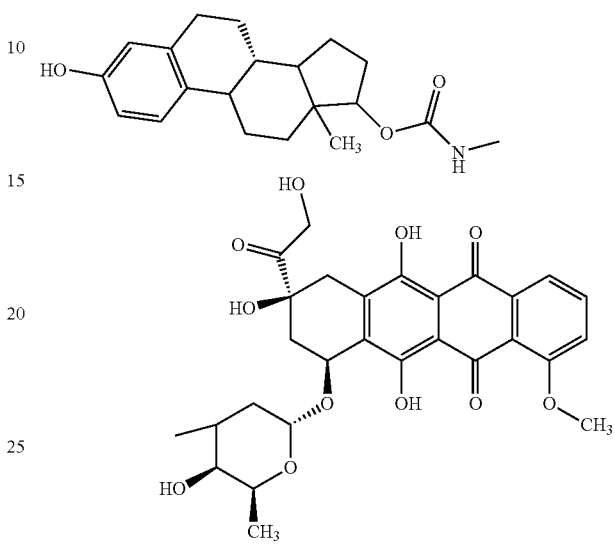

wherein the 3' amino group of doxorubicin is conjugated to estradiol.

In some embodiments, a pharmaceutical compound comprising a compound as defined above and a pharmaceutically acceptable carrier, excipient and/or adjuvant is provided.

Figure 1:
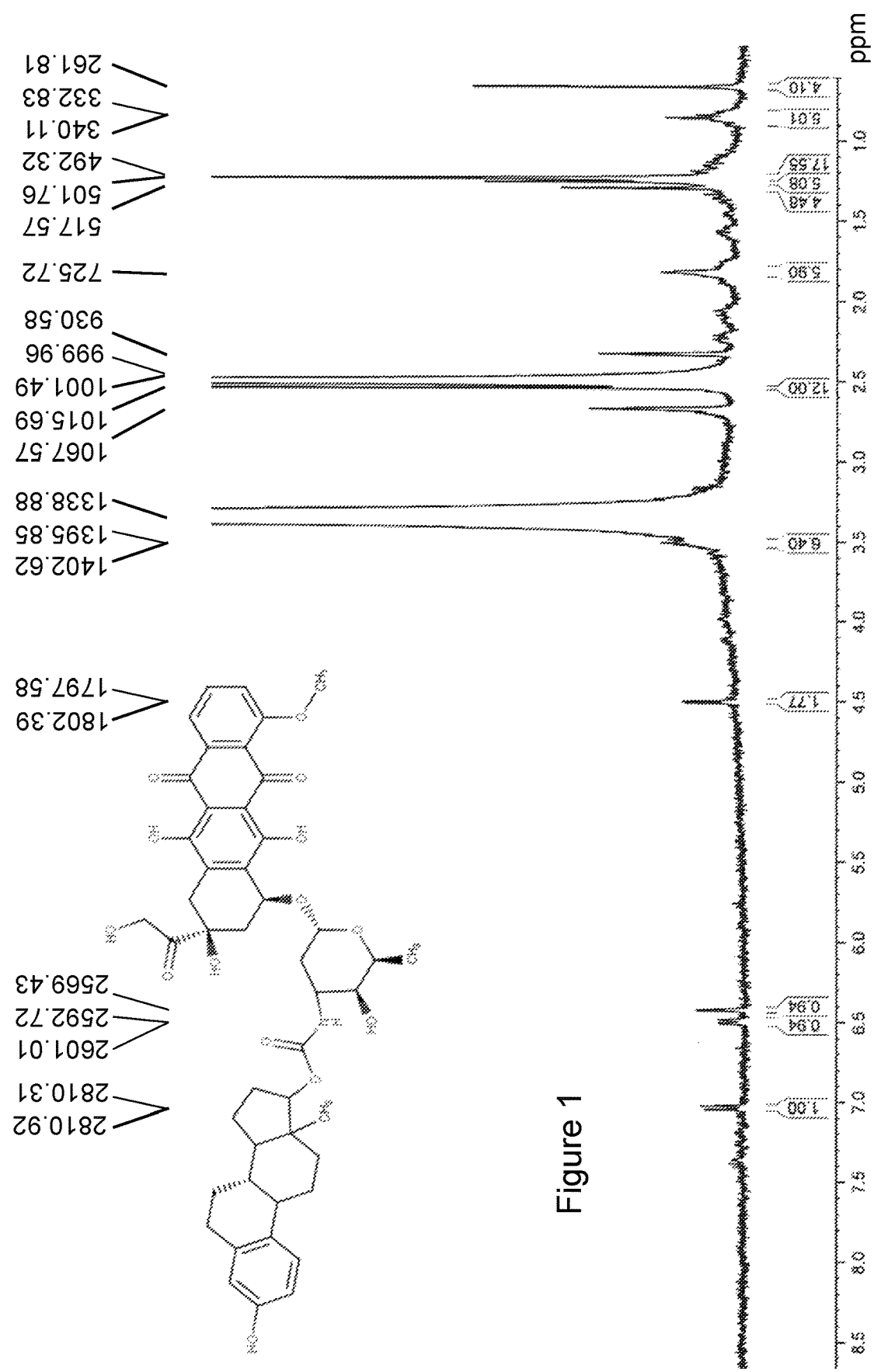
FIG. 1 shows the chemical structure and $^1$H NMR of a disclosed compound, ((3bS)-7-hydroxy-11a-methyl-1H,2H,3H,3aH,3bH,4H,5H,9bH,10H,11H,11aH-cyclopenta[a]phenanthren-1-yl N-[(2S,3S,6R)-3-hydroxy-2-methyl-6-{[(1S,3S)-3,5,12-trihydroxy-3-(2-hydroxyacetyl)-10-methoxy-6,11-dioxo-1,2,3,4,6,11-hexahydrotetracen-1-yl]oxy}oxan-4-yl]carbamate), according to one embodiment of the disclosure.

In one exemplification, the synthesis of the disclosed compound which is a doxorubicn-estradiol conjugate, ((3bS)-7-hydroxy-11a-methyl-1H,2H,3H,3aH,3bH,4H,5H,9bH,10H,11H,11aH-cyclopenta[a]phenanthren-1-yl N-[(2S,3S,6R)-3-hydroxy-2-methyl-6-{[(1S,3S)-3,5,12-trihydroxy-3-(2-hydroxyacetyl)-10-methoxy-6,11-dioxo-1,2,3,4,6,11-hexahydrotetracen-1-yl]oxy}oxan-4-yl]carbamate) utilizes an activation of the hydroxyl group and follows Reaction Scheme A. 17beta-Estradiol (1.36 g, 5 mmol) and 1,1'-Carbonyldiimidazole (0.81 g, 5 mmol) (as disclosed by Greg T. Hermanson., Bioconjugate. 2013, p 229) which were suspended in dimethyl sulfoxide (DMSO) (10 ml). The mixture obtained was incubated to form active substances for 1 hour at room temperature. After 1 hour of incubation, doxorubicin (2.72 g, 5 mmol) was added to the mixtures. Subsequently, all mixtures were incubated at room temperature overnight. The new product was purified by flash chromatography on silica column. A purified was further dried in vacuo, resulting a purple material, the final yield was 3.91 g (79.47%) ES(+)-MS: M-840.3 as shown in FIG. 1.

According to another aspect of the disclosure, the use of the compound as defined above in medicine, such as the use of the embodied compound in a medicament, is provided herein. In some embodiments, the medicament including the compound as defined herein is suitable for treating mammals, such as a human. Moreover, another aspect of the disclosure includes the use of the compound as defined above for the manufacture of a medicament for the treatment of a cancer comprising cancer cells, wherein the examples of the cancer include breast cancer, ovarian, cervical, and other estrogen-receptor-positive (ER+) cancers.

Further examples of the tests of the composition comprising the disclosed compound will now be described.

Figure 2:
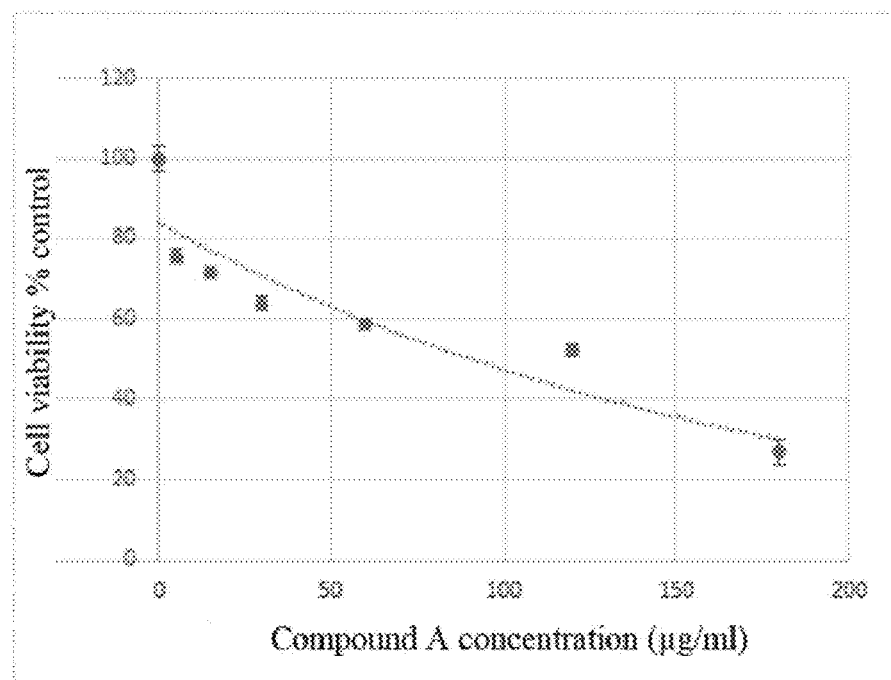
FIG. 2 shows cytotoxicity of a compound according to one embodiment of the disclosure.

Example 1:
3-(4,5-dimethylthiazol-2-yl)-2,5-diphenyl Tetrazolium Bromide (MTT) Assay for Cytotoxicity Effect of Compound A on Tumor Cells The human breast cancer cell line, MCF-7, was obtained from American Type Cell Collection (ATCC) (Rockville, Mo., U.S.A.). The cells were cultured to 70-80% confluence in Dulbecco's modified Eagle medium (DMEM) (Gibco, Grand Island, N.Y., U.S.A.) with 10% fetal bovine serum (FBS) (Gibco) at 37° C. and 5% $CO_2$. MCF-7 cells were plated overnight in a 96-well plate (4,000 cells per well). Cells were treated with compound A at a final concentration 0-180 μg/ml, in triplicate for 24 hours. Next, 10 μl/well of WST-1/ECS solution from the Quick Cell Proliferation Colorimetric Assay Kit (BioVision, Inc., Milptas, Calif., U.S.A.) was added, and the solution was incubated for 2 hours at 37° C. and 5% $CO_2$. Absorbance was measured at 480 nm with the Biochrom Anthos 2010 microplate reader (Biochrom Ltd., Cambourne, Cambridge, UK). The half maximal inhibitory concentrations (IC50s) were calculated from linear regression from the absorbance optical density (OD) of each triplicate concentration. The cytotoxicity is shown in FIG. 2.

Figure 3:
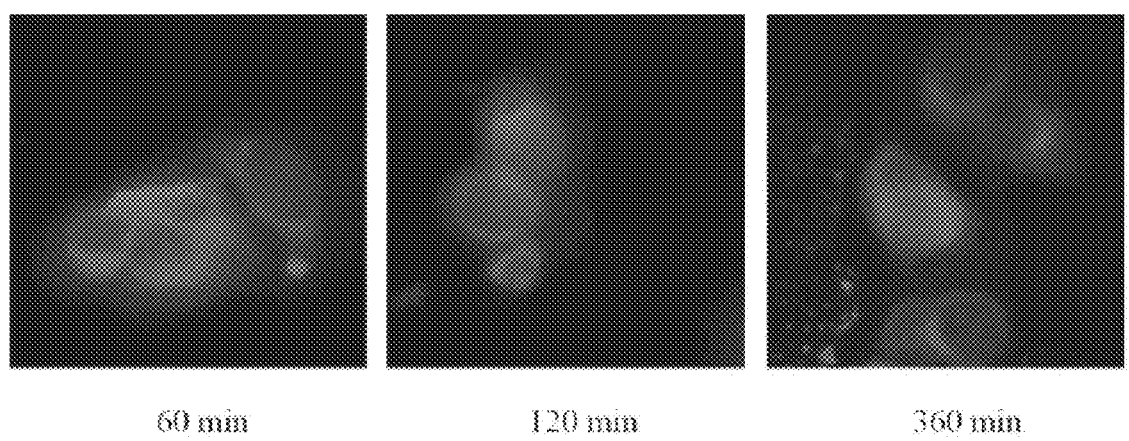
FIG. 3 shows the fluorescent microscopy analysis of the subcellular distribution of the disclosed compound.

Example 2: Fluorescent Microscopy of Subcellular Distribution of the Disclosed Compound Low numbers of MCF-7 cells were seeded into 8-well plate (3,000 cells/well) overnight. During the experiment, culture media was replaced with 10% FBS DMEM added as a supplement, with 120 μg/ml compound A (approximately IC60). Subcellular distribution of compound A in treated cells was observed at 60, 120 and 360 minutes by fluorescent microscopy (Olympus BX51, Tokyo, Japan) and images taken using the Olympus DP71 system are shown in FIG. 3.

Example 3: Lipid Solubility and Oil in Water (O/W) Emulsion Analysis

Figure 4A:
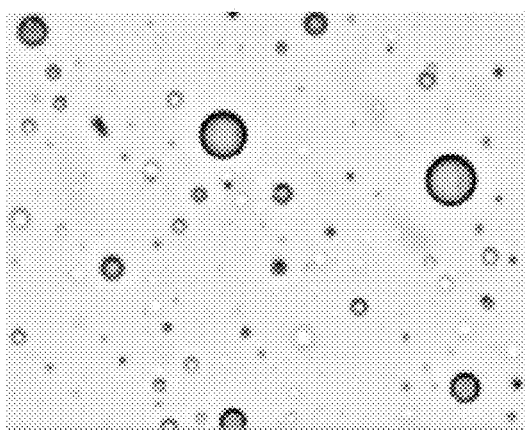
FIG. 4A shows an image of compound A in O/W droplets, visualized under light microscopy.
Figure 4B:
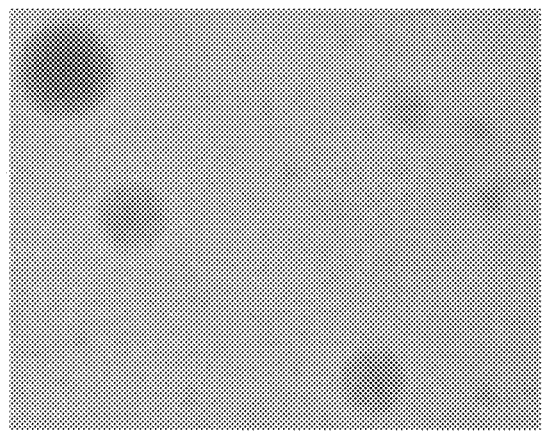
FIG. 4B shows an image of compound A in O/W droplets, visualized under fluorescent microscopy.

Compound A or doxorubicin in DMSO (3 μg/μl) were dissolved in olive oil, canola oil (Sigma-Aldrich (St. Louis, Mo., USA)) and ethiodized oil (Guerbet, Paris, France) at 40° C. The suspended were vortexed and centrifuged at 3000 RPM, 10 mins periodically. Oil solvent volume was step-wise increased till completely soluble was observed and the soluble concentration were determined (Table1). The solutions were left at 24° C. overnight and were centrifuged at 5000 RPM for 20 mins. Ten microliter of compound A in oils were added to 100 μl deionized (DI) water. The suspensions were vigorously vortex and left at room temperature. The distribution of compound A in O/W droplets were visualized under light and fluorescent microscopy (Olympus BX51, Tokyo, Japan) and images taken using the Olympus DP71 system (as shown in FIG. 4). FIG. 4 (*a*) shows an image of compound A in O/W droplets, visualized under light microscopy, and FIG. 4 (*b*) shows an image of compound A in O/W droplets, visualized under fluorescent microscopy.

TABLE 1

| | Solubility in Oil (40° C.) | |
|---|---|---|
| | Disclosed compound (mg/100 ml) | Doxorubicin (mg/100 ml) |
| Olive Oil | 0.0878 | less than 0.0001 |
| Canola Oil | 0.0192 | less than 0.0001 |
| Ethiodized Oil | 0.0411 | less than 0.0001 |

Despite having a lower cytotoxic activity in MCF-7 cells, the conjugated product exerted its actions in a manner that was different to that of DOX. The conjugated product rapidly induced MCF-7 cell apoptosis without entering the nucleus. Further analysis showed that conjugated product increased cytosolic oxidative stress and did not interfere with the cell cycle.

The foregoing description of the present invention has been presented for the purposes of illustration and description. Furthermore, the description is not intended to limit the invention to the form disclosed herein. Consequently, variations and modifications commensurate with the above teachings, and the skill or knowledge of the relevant art, are within the scope of the present invention. The embodiment described hereinabove is further intended to explain the best mode known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

The invention claimed is:

1. A pharmaceutical compound comprising a first component as doxorubicin and a second component as estradiol, wherein the first component is covalently conjugated to the second component having a structure represented by the following chemical formula (I):

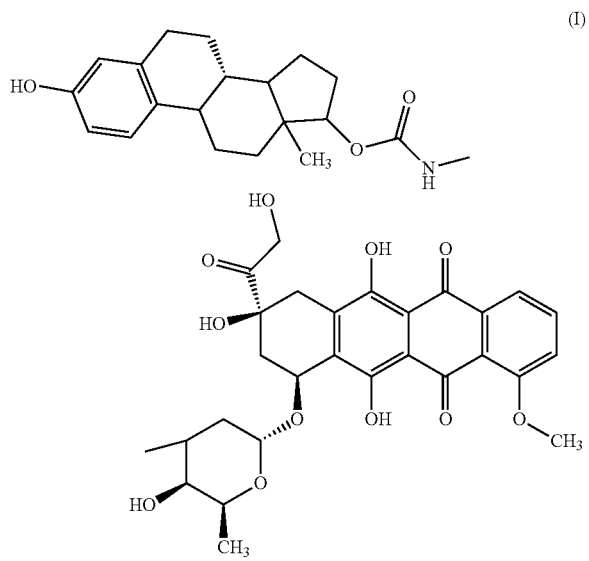

wherein the 3' amino group of doxorubicin is conjugated to estradiol.

2. A pharmaceutical compound comprising a compound as defined in claim 1 and a pharmaceutically acceptable carrier, excipient and/or adjuvant.

* * * * *